United States Patent [19]

Bexten et al.

[11] 4,041,081

[45] Aug. 9, 1977

[54] METHOD FOR THE PREPARATION OF PURE N-ALDEHYDES

[75] Inventors: Ludger Bexten, Kirchhellen; Heinz Noeske, Oberhausen; Hans Tummes, Oberhausen; Boy Cornils, Dinslaken, all of Germany

[73] Assignee: Ruhrchemie Aktiengesellschaft, Oberhausen, Germany

[21] Appl. No.: 637,739

[22] Filed: Dec. 4, 1975

[30] Foreign Application Priority Data

Dec. 14, 1974 Germany .......................... 2459152

[51] Int. Cl.$^2$ ............................................. C07C 47/02
[52] U.S. Cl. .................................. 260/601 R; 260/599
[58] Field of Search ........................ 260/601 R, 599

[56] References Cited

U.S. PATENT DOCUMENTS

| 2,544,562 | 3/1951 | Michael | 260/601 R |
| 2,625,560 | 1/1953 | Michael | 260/601 R |

*Primary Examiner*—James O. Thomas, Jr.
*Assistant Examiner*—W. B. Lone
*Attorney, Agent, or Firm*—Bierman & Bierman

[57] ABSTRACT

A process for the isolation of n-aldehyde from a mixture of n-aldehyde and i-aldehyde in a solvent by the addition of no more than a stoichiometric amount of an alkali metal hydrogen sulfite in aqueous solution to the mixture. The resulting precipitate is separated, washed, and later decomposed to yield substantially pure n-aldehyde.

15 Claims, No Drawings

METHOD FOR THE PREPARATION OF PURE N-ALDEHYDES

The reaction of olefins with carbon monoxide and hydrogen in the presence of catalysts (Hydroformylation or Oxo reaction) results in the formation of aldehydes with an increase of one in the number of carbon atoms. The reaction mixture, which depends on the procedure employed and type of cataylsts used, contains mainly isomeric aldehydes as well as alcohols, esters, hydrocarbons and higher condensation products. The aldehydes obtained by the hydroformylation of terminal olefins are of significant technical and economic importance. Their formation can be represented by the chemical equations below:

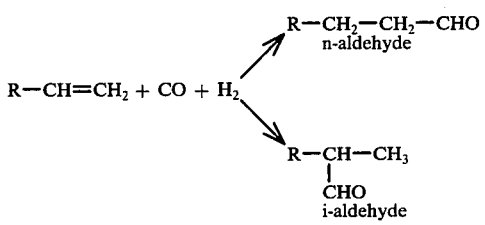

Depending on the reaction conditions, a yield of 30-70% of the valuable unbranched n-aldehyde can be obtained from the hydroformylation of terminal olefins.

There are difficulties encountered in the process of separating the pure n-aldehyde from the isomeric mixture. The low boiling point aldehydes, such as n- and i-butyraldehyde, can be separated by distillation. This method is not possible for purification of the higher boiling point n-aldehydes. The reason for this is that high boiling point isomeric aldehydes have boiling points very similar to one another and thus, high cost distillation methods must be employed. In addition, the high boiling point straight chain aldehydes react, as a result of the thermal conditions, to form aldols or other condensation products with the alcohols available in the crude Oxo product, leading to a loss of the resired substances.

It is therefore an object of the present invention to develop a process for the hydroformylation of terminal olefins which makes possible the isolation of a high purity n-aldehyde with up to 20 carbon atoms from the resulting crude reaction mixture.

According to this invention the problem is solved by a process for separating the pure n-aldehyde with up to 20 carbon atoms from the resulting crude reaction mixture (if necessary catalyst free) of the hydroformylation reaction with terminal olefins. The reaction mixture, in the presence of a solvent, is treated with no more than a stoichiometrical amount of an alkali metal hydrogen sulfite in order to precipitate the n-aldehyde as the hydrogen sulfite addition product. The resulting precipitate is separated, washed and finally decomposed to yield the n-aldehyde.

It is possible, with the help of this new method, to separate n-aldehydes from the corresponding isomeric α-methylaldehydes, as well as from the other compounds which are also present as side products of the hydroformylation of olefins. Basically, this method can be used to separate all Oxo-synthesized aldehydes. It is especially useful, however, in the synthesis of n-aldehydes with 6 or more carbon atoms.

It is known in the prior art, that most aldehydes and aliphatic ketones, whose carbonyl groups are not too strongly blocked by α-substituents, readily add hydrogen sulfite exothermally. It is also true, however, that the effectiveness of the blocking increases with the bulkiness of the neighboring groups. Small alkyl groups, therefore, do not impair the formation of the hydrogen sulfite addition product.

It is therefore not be expected from consideration of the above that a methyl group in the α-position to the carbonyl group would provide a blocking effect and thus markedly reduce the stability as well as rate of formation of the isoaldehyde hydrogen sulifte compound. This discovery now permits a selective separation of n-aldehydes from n-aldehyde/iso-aldehyde mixtures. The resulting crude reaction mixture can be directly employed and separation of the catalyst is not necessary. This is especially true for the cases in which the Oxo reaction is carried out in the presence of small amounts of catalyst (e.g. as is customary with rhodium). The new method can, of course, be used for n- /i-aldehyde mixtures from other sources.

The reaction between the aldehyde and alkali metal hydrogen sulfite goes to completion at temperatures between room temperature and 130° C. The chosen temperature is set according to the rate of formation as well as the thermal stability of the n-aldehyde hydrogen sulifite addition product. The process can be easily conducted if the aldehyde mixture is brought into contact with the alkali metal hydrogen sulfite solution whereby an initmate mixing of the organic and aqueous phases takes place. The hydrogen sulfite addition product precipitates at this point in crystalline form and can be separated by filtration from the two phase system.

If the precipitation occurs by the slow addition of a concentrated sodium hydrogen sulfite solution to the aldehyde dissolved in a solvent, there is obtained a coarse, crystalline, easily filterable precipitate. Low boiling point inert liquids, such as water, alcohols, ethers, aliphatic and aromatic hydrocarbons are suitable solvents. They can also be used to wash out the filtered precipitate. The alkali metal hydrogen sulfite in aqueous solution is employed in stoichiometric amounts, or preferably 70-95% of the theoretical amount required to react with the n-aldehyde. The less the amount of hydrogen sulfite used, the higher the purity of the separated n-aldehyde.

A variation of the process of the present invention can be employed wherein the main part of the n-aldehyde is separated using less than the theortical amount of hydrogen sulfite, yielding a highly pure hydrogen sulfite addition product from the isomeric mixture. The remaining n-aldehyde in the filtrate is obtained by further precipitation. In this case, an amount of hydrogen sulfite is used in excess of that theoretically needed to react with the n-aldehyde remaining in the filtrate, and a precipitate consisting of approximately 50% n-aldehyde hydrogen sulfite and approximately 50% iso-aldehyde hydrogen sulfite addition product is obtained. This precipitate can be used together with an alkali metal hydrogen sulfite in aqueous solution for the partial precipitation of the n-aldehyde from the isomeric mixture, as the i-aldehyde addition product reacts with the n-aldehyde forming n-aldehyde addition product and freeing the i-aldehyde.

The decomposition of the n-aldehyde hydrogen sulfite compound takes place smoothly at temperatures between 50° and 100° C by adding a carbonyl compound with one to four carbon atoms in the molecule. Formaldehyde, n-butyraldehyde and i-butyraldehyde are suitable, as their sulfite compounds dissolve well in water and can be thus easily removed from the decomposition product by extraction with water.

After the decomposition, the n-aldehyde precipitates, and is in an impure state due to the presence of the solvent used for the washing of he hydrogen sulfite precipitate and the aldehyde used in excess for the decomposition. These impurities can be easily removed from the crude n-aldehyde by distillation as an azeotrope with water. In order to obtain the substantially pure aldehyde the small amount of the remaining high boiling polymer aldehydes must be finally separated by distillation.

EXAMPLE 1

The resulting crude product from the hydroformylation of styrene in the presence of rhodium was used as starting material. It consisted of 7.1% styrene and ethylbenzene, 41.2% 2-phenylpropanal-1, 47.2% 3-phenylpropanal-1, 2.5% phenylpropanol, and 2% higher boiling substances. 300 g of the crude Oxo product and 600 g of benzene were intoduced into a 2 liter three necked flask equipped with a stirrer, a dropping funnel, and an attachment for a thermometer and $N_2$ protection. 366 g of 30% aqueous $NaHSO_3$ solution (corresponding to a stoichiometric amount of $NaHSO_3$ required to reach with 3-phenylpropanal-1) were added dropwise at 50° C over a period of 60 minutes. After the flask contents cooled to room temperature, the coarse crystalline slurry was separated and washed with benzene. 13.5% 2-phenylpropanal-1 and 1.3% 3-phenylpropanal were present in the filtrate which totaled 711g. For the decomposition, the hydrogen sulfite precipitate was mixed with 158 g of 30% formalin solution and heated. At 85° C the decomposition was completed in approximately one hour. After removing the aqueous phase, the organic phase was washed three times with 100 ml of water. An organic product (185 g) was obtained, which consisted of 29.2% benzene, 0.8% formaldehyde, 0.6% 2-phenylpropanal-1, 68.1% 3-phenylpropanal-1 and 1.3% polymerization products. A yield of 89% was attained with respect to the amount of 3-phenylpropanal-1.

EXAMPLE 2

The conversion was carried out in manner analogous to that of Example 1, except that only 90% of the stoichiometrical amount of $NaHSO_3$ (based on the amount required to react with 3-phenylpropanal-1) was used for hydrogen sulfite preciptation at a reaction temperature of 70° C. 150 g of the organic product was obtained after decomposition with formaldehyde and consisted of 17.1% benzene, 0.4% formaldehyde, 0.3% 2-phenylpropanal-1, 79.6% 3-phenylpropanal-1, and 2.6% polymerization products. An 84% yield of phenylpropanal-1 was attained.

EXAMPLE 3

The resulting product of the hydroformylation of unbranched $\alpha$-$C_{10}$-olefins (in the presence of rhodium) was used as starting material. It consisted of 2.4% hydrocarbons, 44.6% iso-$C_{11}$-aldehyde, 49.4% n-$C_{11}$-aldehyde, 1.7% formic acid ester, 0.6% $C_{11}$-alcohols and 1.3% higher boiling substances. 300 g of the crude Oxo product and 600 g of benzene were introduced into a 2 liter three necked flask equipped with a stirrer, a dropping funnel and an attachment for a thermometer and $N_2$ protection. 287 g of 30% aqueous $NaHSO_3$ solution were added dropwise within 60 minutes at 50° C (corresponding to 95% of the stoichiometrical amount of $NaHSO_3$ required to react with the n-$C_{11}$ aldehyde). After the flask contents had cooled to room temperature, the crystalline slurry was separated and washed with benzene. 13.0% iso-$C_{11}$-aldehyde and 2.9% n-$C_{11}$-aldehyde were in the filtrate which totaled 704 g. 130 g of a 30% formalin solution were mixed with the dried hydrogen sulfite precipitate and the decomposition. At 90° C the decomposition was accomplished in approximately one hour. After removing the aqueous phase, the organic phase was washed three times with 100 ml water. 132 g of an organic product was obtained consisting of 3.7% benzene, 0.8% formaldehyde, 1.0% i-$C_{11}$-aldehyde, 961% n-$C_{11}$-aldehyde and 3.4% condensation products. A yield of 81% was attained with respect to the n-$C_{11}$-aldehyde.

In further experiments, methanol, isopropanol, isooctane and cyclohexane were used instead of benzene for the precipitation and washing of the precipitate. In these cases comparable results were obtained.

EXAMPLE 4

The conversion was carried out in a manner analogous to that of Example 3, except that the hydrogen sulfite precipitation was conducted in the presence of water was reaction medium. The precipitate was removed by centrifugation. Three phases were formed; the precipitate at the bottom, the clear aqueous phase in the middle, and a slightly turbid organic phase on top. The liquid was decanted from the precipitate and aqueous and organic phases separated. The organic phase (151 g) contained 72.3% i-$C_{11}$-aldehyde as well as 12.7% n-$C_{11}$-aldehyde.

The precipitate was decomposed with a 30% formalin solution. 128 g of an organic product was obtained which consisted of 1.3% formaldehyde, 0.1% intermediate runnings, 6.7% i-$C_{11}$-aldehyde, 90.1% n-$C_{11}$-aldehyde, 0.1% formic acid ester and $C_{11}$-alcohols, and 1.7% condensation-products.

EXAMPLE 5

The conversion was carried out in a manner analogous to that of Example 3, except that the hydrogen sulfite precipitation was conducted in isopropanol. The filtered precipitate was washed with 500 g of water and two phases (an upper organic and a lower aqueous phase) were present in the filtrate. The aqueous phase was separated and used several times to wash out the precipitate. The organic phase (13 g) contained 27.9% isopropanol, 2.6% $C_{10}$-hydrocarbons, 54.9% iso-$C_{11}$-aldehyde, 14.0% n-$C_{11}$-aldehyde and 0.6% $C_{11}$-alcohols and higher boiling point substances.

The amount of impure substances present in the precipitate was determined in the followng manner. 150 g of isopropanol was added to the precipitate and then removed. This operation was performed three times. The filtrate containing isopropanol and the impure substances was tested. The results showed that the precipitate contained less than 0.1% of impure substances.

EXAMPLES 6 & 7

In these examples, the procedure as shown in Example 3 was used except that the decomposition of the hydrogen sulfite compound was carried out with n-butyraldehyde or iso-butyraldehyde in the presence of 600 g of water. The conversion was completed within 2 hours at 70–80° C with 120 g of n-butyraldehyde (200% of the theoretical) and within 4 hours at 60–65° C with 180 g of isobutyraldehyde (300% of he theortical).

EXAMPLE 8

The product resulting from the hydroformylation of a $C_{12/14/16}$ olefin mixture (in the presence of rhodium) was used as the starting material. It consisted of 8.1% hydrcarbons, 18,0% iso-$C_{13}$-aldehyde, 29.2% n-$C_{13}$-aldehyde, 11,9% iso-$C_{15}$-aldehyde, 11.8% n-$C_{15}$-aldehyde, 0.4% iso-$C_{17}$-aldehyde, 0.4% n-$C_{17}$-aldehyde, 2.2% ester and 5.0% $C_{13/15}$-alcohols and 13.0% non identified components.

1000 g of a crude Oxo product and 3000 g of isopropanol were introduced into a 6 liter three necked flask. 600 g of a 30% aqueous $NaHSO_3$ solution (corresponding to 95% of the stoichiometrical amount of $NaHSO_3$ required for reaction with the n-aldehyde) were added dropwise over 60 minutes at 50° C. 347 g of an organic product was obtained after decomposition of the precipitate with 260 g of a 30% formalin solution. It consisted of 1.5% formaldehyde, 0.6% isopropanol, 3.1% i-Chd 13-aldehyde, 67.5% n-$C_{13}$-aldehyde, 2.7% i-$C_{15}$-aldehyde, 23.8% n-$C_{15}$-aldehyde and 0.8% n-$C_{17}$-ldehyde.

What is claimed is:

1. A process for the isolation of n-aldehyde from an organic solution containing n-aldehyde and i-aldehyde obtained by the reaction of an olefin with carbon monoxide and hydrogen in the presence of a catalyst at a reaction temperature between room temperature and 130° C. by adding no more than a stoichiometric amount based on said n-aldehyde of an alkali metal hydrogen sulfite in aqueous solution to said organic solution whereby a preciptate of n-aldehyde hydrogen sulfite is formed, and removing said n-aldehyde from said preciptate.

2. The process of claim 1 wherein said n-aldehyde contains at least six carbon atoms.

3. The process of claim 1 wherein said amount of alkali metal hydrogen sulfite in aqueous solution is 70–95% of said stoichiometric amount.

4. The process of claim 1 wherein said alkali metal hydrogen sulfite is sodium hydrogen sulfite.

5. A process for the isolation of n-aldehyde from an organic solution comprising n-aldehyde and i-aldehyde in a solvent obtained by the reaction of an olefin with carbon monoxide and hydrogen in the presence of a catalyst, said process comprising:
   a. forming a reaction mixture at a reaction temperature of between room temperature and 120° C. by adding no more than a stoichiometric amount based on said n-aldehyde of alkali metal hydrogen sulfite in aqueous solution to said organic solution whereby a precipitate of n-aldephyde hydrogen sulfite is formed.
   b. separating said precipitate from reaction mixture, and
   decomposing said precipitate at a temperature between 50° C. by adding a carbon compound, having one to four carbon atoms to said precipitate, and compound having a greater affinity for hydrogen sulfite than said n-aldehyde, whereby an n-aldehyde is obtained.

6. The process according to claim 5 comprising washing said precipitate with a substance selected from the group consisting of water, alcohols, ethers, aliphatic hydrocarbons, and aromatic hydrocarbons.

7. The process according to claim 6 comprising removing the excess of said substance and said compound to obtain purified n-aldehyde.

8. The process of claim 5 wherein said solvent is selected from the group consisting of water, alcohols, ethers, aliphatic hydrocarbons, and aromatic hydrocarbons.

9. The process of claim 5, wherein said amount of alkali metal hydrogen sulfite 70–95% of said stoichiometric amount.

10. The process of claim 5, wherein said compound is selected from the group consisting of formaldehyde, n-butyraldehyde, and i-butyraldehyde.

11. The process of claim 7 comprising removing said excess by distillation as an azeotrope with water and then removing remaining high boiling polymer aldehydes by further distillation.

12. The process of claim 5 wherein said n-aldehyde contains at least 6 carbons atoms.

13. The process of claim 5 wherein said alkali metal hydrogen sulfite is sodium hydrogen sulfite.

14. The process of claim 13 wherein said n-aldehyde contains at least 6 carbons atoms and said amount of alkali metal hydrogen sulfite is 70–95% of said stoichiometric amount.

15. The process of claim 5 further comprising:
   a. adding less than said stoichiometric amount of said alkali metal hydrogen sulfite to said organic solution,
   b. separating a first precipitate from said reaction mixture,
   c. adding an amount of said alkali metal hydrogen sulfite in aqueous solution to said organic solution to obtain a secnd precipitate, said amount being greater than the theoretical amount required to react with the n-aldehyde remaining in the reaction mixture, said secnd precipitate comprising n-aldehyde hydrogen sulfite and i-aldehyde hyfrogen sulfite,
   d. adding alkali metal hydrogen sulfite in aqueous solution and said second precipitate to said organic solution to obtain a third precipitate comprising n-aldehyde hydrogen sulfite, and
   e. separating said third precipitate from said reaction mixture.

* * * * *